United States Patent [19]

Kelly et al.

[11] 4,104,013
[45] Aug. 1, 1978

[54] TAMPON EJECTOR TUBE AND APPARATUS

[75] Inventors: Eugene R. Kelly, Hauppauge; Donald M. Gould, Glen Cove, both of N.Y.

[73] Assignee: Product Design & Engineering Corp., Minneapolis, Minn.

[21] Appl. No.: 654,378

[22] Filed: Feb. 2, 1976

[30] Foreign Application Priority Data

Aug. 7, 1975 [GB] United Kingdom ............... 28706/75

[51] Int. Cl.² .......................................... B29C 17/00
[52] U.S. Cl. ................................ 425/324.1; 425/340; 425/355; 425/393
[58] Field of Search .................. 425/324 R, 343, 341, 425/393, 317, DIG. 201, 436 R, 352–355

[56] References Cited

U.S. PATENT DOCUMENTS

| 3,034,172 | 5/1962 | Sander et al. | 425/393 |
| 3,475,786 | 11/1969 | Pearson | 425/393 X |
| 3,484,900 | 12/1969 | Sands et al. | 425/393 |
| 3,806,301 | 4/1974 | Osterhegen et al. | 425/393 |
| 3,877,282 | 4/1975 | Pogonowski | 425/393 X |
| 3,923,443 | 12/1975 | Emerg et al. | 425/393 X |
| 3,932,094 | 1/1976 | Korff et al. | 425/393 |
| 3,961,113 | 6/1976 | Marco | 425/393 |

Primary Examiner—Robert L. Spicer, Jr.
Attorney, Agent, or Firm—Bauer, Amer & King

[57] ABSTRACT

An apparatus and method are disclosed for forming an improved ejection (inner) tube for use in a telescoping tampon applicator. The apparatus and method takes a tubular blank and, in one step, provides an improved ejection tube by forming simultaneously a bead-like rim on one end of the tube, an inwardly turned bearing surface on the other end of the tube, and a plurality of outwardly projecting abutments on the surface of the tube near the bearing surface end thereof.

11 Claims, 18 Drawing Figures

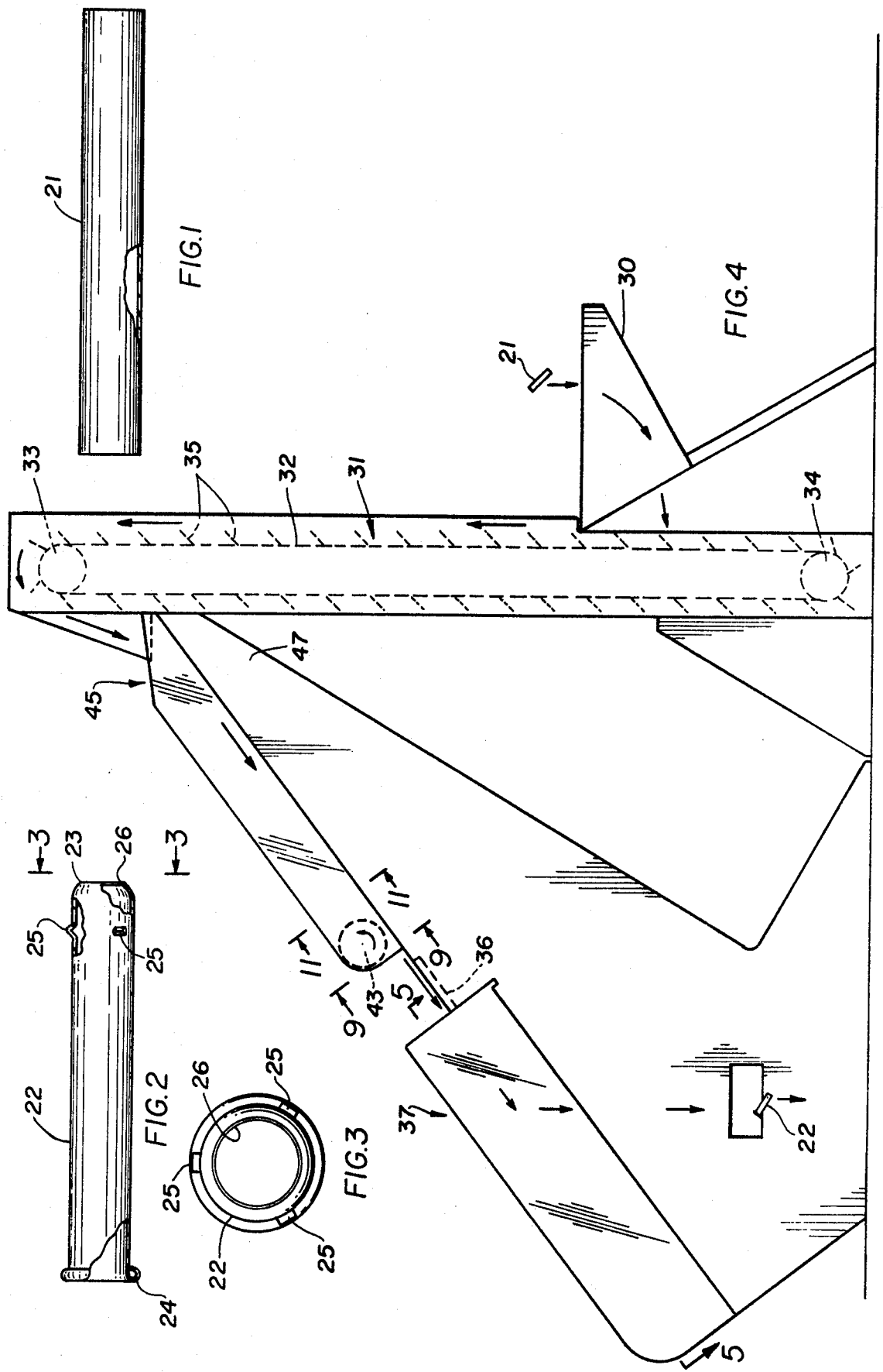

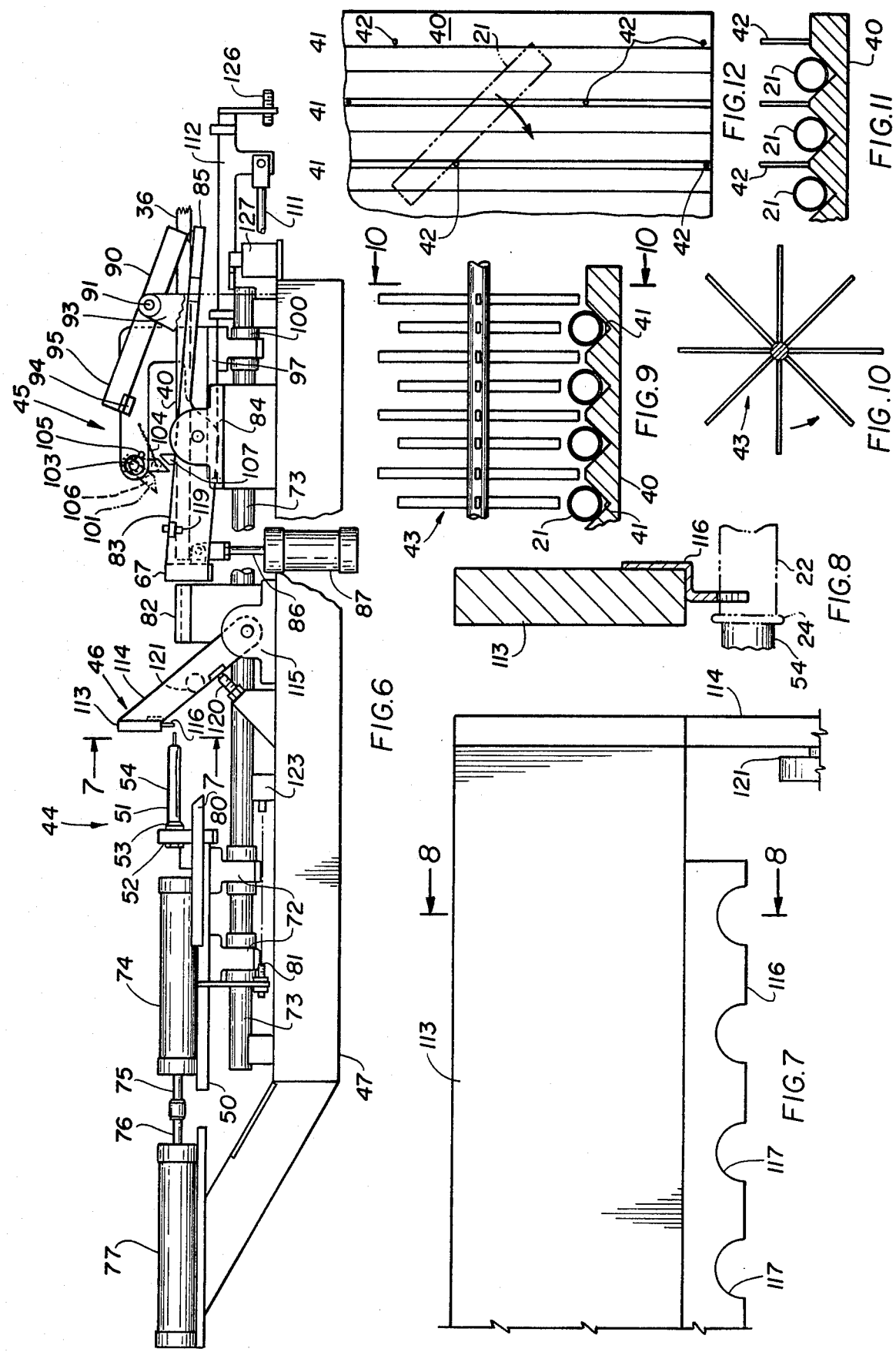

4,104,013

TAMPON EJECTOR TUBE AND APPARATUS

BACKGROUND OF THE INVENTION

The invention relates to a tube forming apparatus and method, and more particularly to an apparatus and method for forming a tampon ejector tube provided for a telescoping tampon applicator.

The general arrangement and configuration of tampon applicators are well known in the art so that it will suffice for purposes of this description simply to note that such applicators consist of a carrier tube in which a tampon is positioned to be ejected by a tube that initially projects from the carrier tube but which pushes the tampon from the carrier tube when the ejector tube is telescoped within the carrier tube.

While tampon applicators have remained basically unchanged since the introduction of such devices, the carrier tube especially has become highly developed over the years. For example, as the materials suitable for use in the carrier tube have changed to thin walled flexible plastics, the tube has been provided at its remote end with a comparatively firm or riged gripping ring. Also, to facilitate comfortable and easy entry of the applicator into a body cavity, the forward end of the tube is generally a closed curved surface of revolution which is provided with intersecting radial slits that permit the surface to fold outwardly to allow the exit of a tampon from the tube. The ejector tube has remained essentially that, a straight tubular member with an inwardly inclined forward end that can engage and eject a tampon when the tube is telescoped within the carrier tube. The ejector tube is also provided with abutments on its outer surface that cooperate with detents on the inside surface of the carrier tube to obviate the inadvertent withdrawal and separation of the ejector tube from the carrier tube.

SUMMARY OF THE INVENTION

It is the object of the invention to provide an improved apparatus for shaping tampon applicator ejector tubes.

It is another object of the invention to provide an apparatus for forming ejector tubes at a high rate of production.

It is still another object of the invention to provide an apparatus for forming a plurality of ejector tubes simultaneously.

It is yet another object of the invention to provide an apparatus and method in which a straight tubular blank is formed into an ejector tube having both ends conformed to a desired shape and abutments formed on the outside surface near one end of the ejector tube in a single forming operation.

It is also an object of the invention to provide an improved ejector tube which is devoid of sharp edges that might otherwise be encountered by a user of a tampon applicator.

In carrying out the present invention, there is provided an apparatus comprising a hopper for receiving a supply of short tubular blanks, an elevator mechanism for carrying the blanks from a hopper discharge port to a downwardly inclined sorting and arranging table that aligns the blanks in a plurality of parallel gravity feed channels, a feed mechanism for simultaneously advancing one blank from each feed channel to a forming mechanism, a mechanism for simultaneously forming each blank fed thereto into a tampon applicator ejector tube, and a stripper device for removing an ejector tube from the forming mechanism.

A feature of the invention is that it provides an apparatus for manufacturing improved tampon applicator ejector tubes at low cost and at a high rate of production.

Another feature of the invention is that it provides an apparatus that simultaneously produces a plurality of tampon applicator ejector tubes.

Other features and advantages of the invention may be gained from the foregoing and from the description of a preferred embodiment of the invention which follows.

DESCRIPTION OF THE DRAWING

In the drawing:

FIG. 1 is an elevational view of a tubular blank that is to be formed into a tampon applicator ejector tube;

FIG. 2 is a front elevational view, partly in section, showing a tampon applicator ejector tube;

FIG. 3 is a right side elevational view of the ejector tube of FIG. 2;

FIG. 4 is a front elevational view showing schematically the arrangement of the component parts of the apparatus of the present invention;

FIG. 6 is a side elevational view of the mechanism shown in FIG. 5, taken along line 6—6 of FIG. 5;

FIG. 7 is a fragmentary view of the stripper mechanism taken along line 7—7 of FIG. 6;

FIG. 8 is a sectional view taken along line 8—8 of FIG. 7;

FIG. 9 is a fragmentary elevational view taken along line 9—9 of FIG. 4;

FIG. 10 is a side elevational view taken along line 10—10 of FIG. 9;

FIG. 11 is a fragmentary sectional view of the sorting and arranging table taken along line 11—11 of FIG. 4;

FIG. 12 is a plan view of the fragment of the sorting and arranging table shown in FIG. 11;

DETAILED DESCRIPTION OF THE INVENTION

Figure 5:
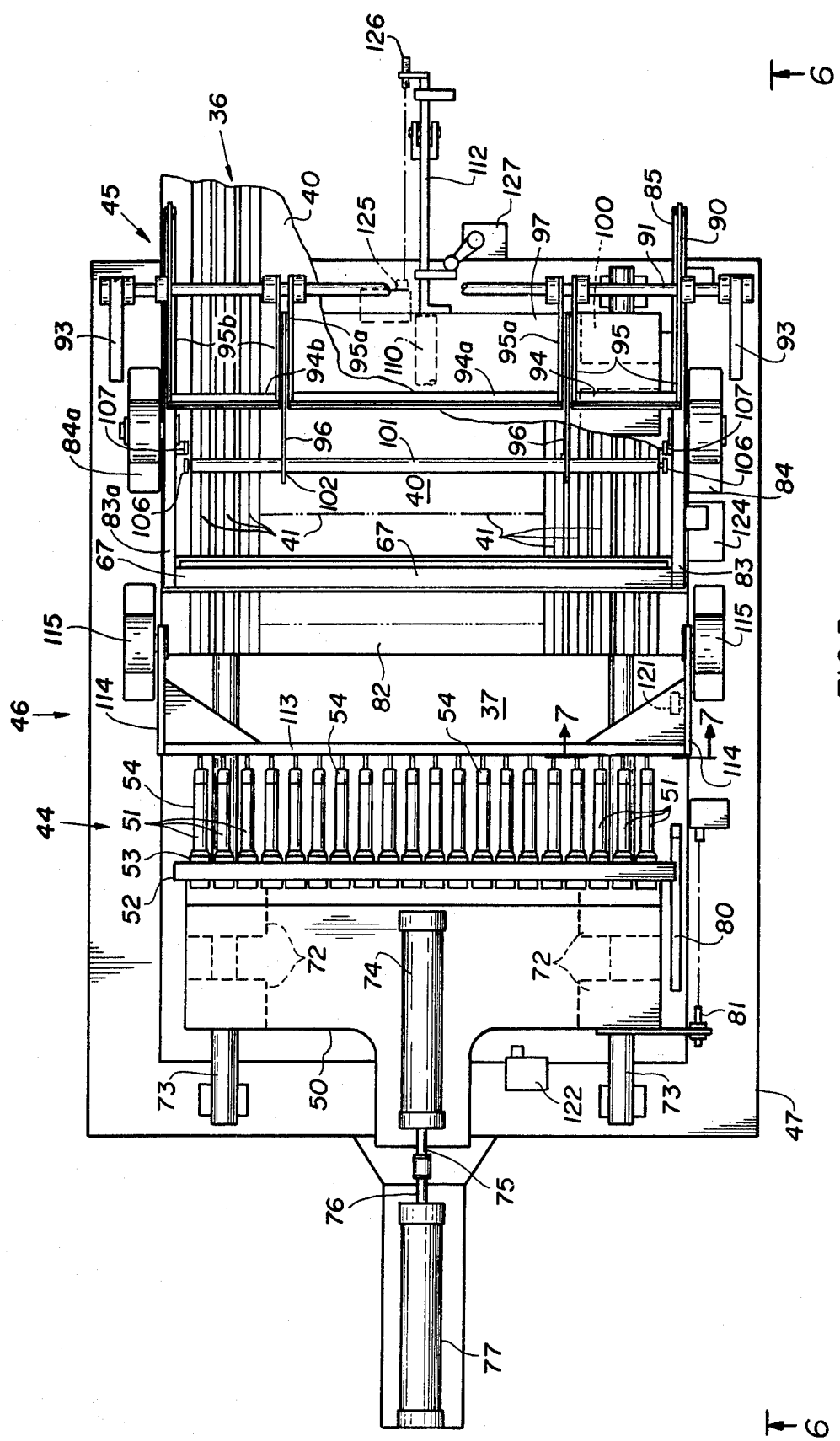
FIG. 5 is an oblique view of a portion of the blank sorting and arranging table, the feeding mechanism, the forming mechanism, and the stripper mechanism of the apparatus, taken along line 5—5 of FIG. 4.

Reference is now made to the drawing and initially to FIG. 1 which shows a tubular blank 21 from which a tampon applicator ejector tube 22 (FIGS. 2 and 3) is formed. The blank 21 is preferably of a plastic material and itself is formed in an extrusion molding apparatus that produces endless tubing which is severed into segments equal in length to that of blank 21. The tubing and blanks 21 formed therefrom have a relatively thin wall which permits radial deformation although the blanks are rigid in a longitudinal direction.

The applicator ejector tube 22 shown in FIGS. 2 and 3 is slightly shorter in length than blank 21 due to the distal end 23 of tube 22 being curved inwardly and the proximate end of the tube being shaped into a semi-circular rim or bead 24 as shown. Tube 22 also is provided with a plurality of abutments 25 spaced around the outer periphery of the tube near its distal end. These abutments co-act with detents formed on the inner surface of a tampon carrier tube to prevent tube 22 being inadvertently withdrawn from the carrier tube when the two are assembled together prior to use as a tampon applicator. Instead of providing tube 22 with spaced abutments 25, an annular ridge could serve the same purpose provided the carrier tube is formed accordingly.

The distal end of tube 22 is curved inwardly a distance sufficient to provide an adequate surface area to bear against a tampon and push or eject it from a carrier tube. However, the distal end of tube 22 cannot be completely closed but must be provided with an aperture 26 since a string normally provided to facilitate withdrawal of a tampon from a body cavity will initially pass through aperture 26 and tube 22 with its loose end adjacent the proximate end of tube 22. The semi-circular rim 24 provided at the proximate end of tube 22 enables a tampon applicator user to press on that end of tube 22 and not encounter a sharp edge as would be the case if the end of blank 21 was not finished as illustrated.

Having thus described the ejector tube 22, attention can be directed to the apparatus provided according to the present invention for forming such tubes. In FIG. 4, the general configuration of the apparatus is schematically shown to illustrate the functional components of the apparatus and their orientation to each other. A plurality of blanks 21 are introduced into a hopper 30 which discharges them onto an elevator mechanism 31 that carries the blanks to the top of the apparatus. The elevator mechanism 31 is in the form of an endless conveyor belt 32 trained over an upper elongated pulley 33 and a similar lower pulley 34, one of which will be power driven to provide motive power to the belt 32. The outer surface of belt 32 is provided with slats 35 that serve as buckets to carry blanks 21 received from hopper 30 to the elevated position shown. As conveyor belt 32 passes over top pulley 33, slats 35 are inverted and the blanks 21 carried thereby are randomly deposited at the top of a sorting table 36. Hopper 30, its discharge port, and elevator mechanism 31 are as wide as table 36 so that blanks 21, when spilled onto sorting table 36, are distributed across the full width of the table.

Sorting table 36 and the ejector tube forming mechanism 37 are inclined downwardly and away from elevator mechanism 31 with the result that blanks 21 deposited by the elevator mechanism on the sorting table move under the force of gravity along table 36 to mechanism 37 and, after being formed into ejector tubes 22, to a collection bin (not shown). As will be seen in the following detailed description of table 36 and mechanism 37, a feed mechanism is provided to feed blanks 21 one at a time to forming mechanism 37.

Attention is now directed to FIGS. 9 to 12. Sorting table 36 comprises an essentially flat rectangular member 40 having a plurality of parallel triangularly shaped channels 41 formed in the upper surface of the table. The channels extend longitudinally along the entire length of the table and serve to guide blanks 21 from elevator mechanism 31 to the ejector tube forming mechanism 37. Instead of being a flat member with channels provided therein, table 36 could be formed of a corrugated piece of sheet metal. Since blanks 21 are deposited on table 36 in a random fashion, means are provided to orient and align the blanks with channels 31 so that the blanks fall into the channels for movement to forming mechanism 37. Such means take the form of upright pins 42 set on the flat surfaces separating channels 41. Any blanks moving down the inclined table 36 transverse to channels 41 will strike a pin 42 and be pivotted thereby into alignment with and into a channel 41. See FIG. 12. Also, since blanks 21 are being randomly deposited on table 36, it could occur that blanks reach the exit end of the table one on top of another, or in other words, in a double layer. To avoid such an occurrence, a brush 43 rotating in a counterclockwise direction (FIG. 4) is provided to propel such excess blanks back up the table where they will again have an opportunity to find a position in a channel 41. Of course, the rate at which blanks are deposited on table 36 will be controlled to equal the number of blanks that can be formed in forming mechanism 37 in a given time period. Under such circumstances, each channel 41 of sorting table 36 will have a plurality of aligned blanks awaiting feed to forming mechanism 37. In this way, each forming device (one device is provided in alignment with each channel 41) will receive a blank for forming during each cycle of operation of the forming mechanism.

Attention is now directed to FIGS. 5 and 6 of the drawing which show the ejector tube forming mechanism 44, the blank feeding mechanism 45 that delivers one blank at a time to each unit of forming mechanism 44, and the stripping mechanism 46 that removes the formed ejector tubes 22 from the forming mechanism 44. These mechanisms, 44, 45, and 46, are shown mounted on a machine frame 47 which provides a rigid base for the several assemblies.

Forming mechanism 44 comprises a carriage 50 on which are mounted a plurality of forming units 51 each aligned with a channel 41 of sorting table 36. The number of forming units provided depends simply on the desired production capacity of the apparatus, but the present invention contemplates the provision of approximately twenty forming units per apparatus. Each forming unit 51 is mounted on a carriage bracket 52 and comprises a heated die 53 with an integral mandrel 54 projecting therefrom.

Figure 15:
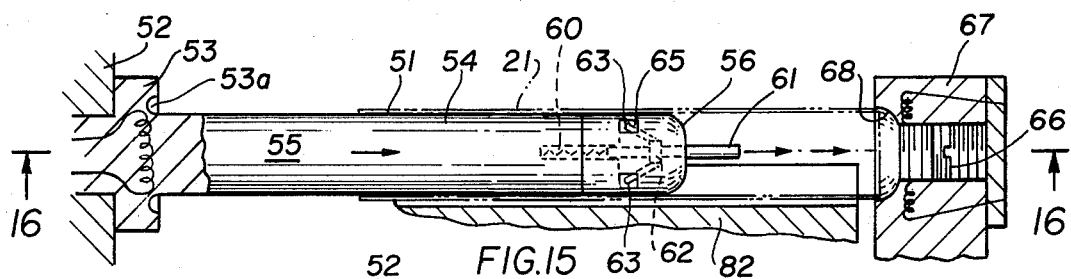
FIG. 15 is a fragmentary view, partly in section, of the forming mechanism of the apparatus of the invention.
Figure 16:
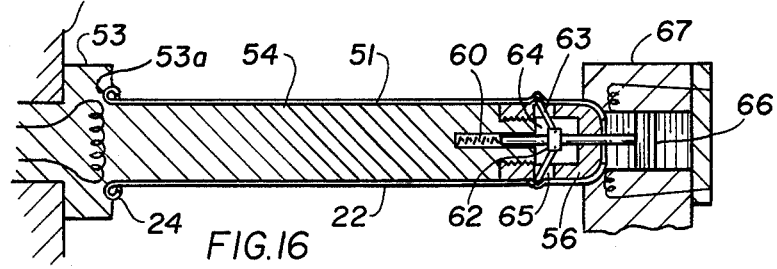
FIG. 16 is a view of the forming mechanism of FIG. 15 showing the relationship of parts during a forming operation.

Referring to FIGS. 15 and 16, which show a forming unit 51 in more detail, blank supporting mandrel 54 comprises two parts 55 and 56, the latter of which carries means for forming abutments 25 on an ejector tube 22. The abutment forming means comprise a pin 61 to which is keyed a collar 62 and a plurality of radially extending arms pivotally connected to the collar. Pin 61 is biased to the right by compression spring 60. It will be arrested in its rightward position by the engagement of collar 62 with the right end wall of chamber 64. At such time, radial arms 63 will be withdrawn within part 56. Pin 61 will be moved leftwardly (FIGS. 15 and 16) and arms 63 will project through apertures 65 to form abutments 25 when pin 61 strikes stop screw 66 in fore die 67 as mandrel 54 moves into die 67 to form end 23 of tube 22. The position of screw 66 is adjustable to control the leftward movement of pin 61 and the consequent extension of arms 63 and projection of abutments 25. Pin 61 will again move to the right and be restored to its normal position (FIG. 15) and arms 63 will be withdrawn within part 56 when movement of mandrel 54 away from die 67 permits spring 60 to urge it rightwardly.

Figure 17:
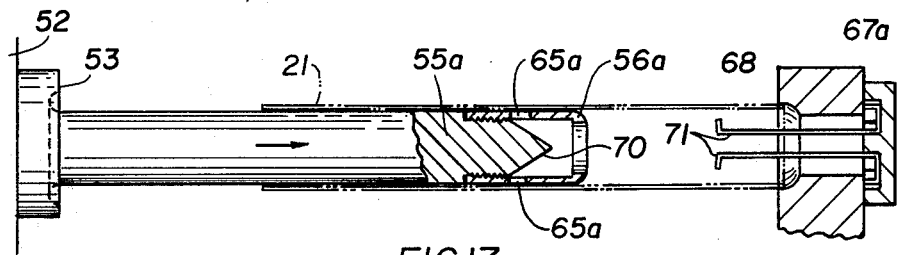
FIG. 17 is a view similar to FIG. 15 but illustrating a different embodiment of the forming mechanism.
Figure 18:
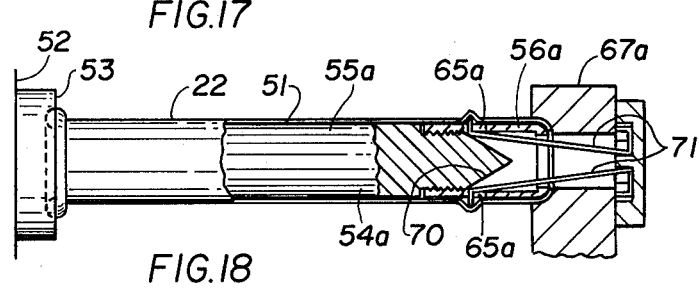
FIG. 18 is a view similar to FIG. 16, but illustrating the embodiment of FIG. 17.

Another embodiment of mandrel 54 is shown in FIGS. 17 and 18. Here again, the mandrel comprises two parts, 55a and 56a. Part 55a is provided at its forward end with a conical cam 70 and part 56a is a cup-shaped element with a central aperture in its end wall and a plurality of apertures 65a spaced around its side wall. The abutment forming means comprises a plurality of spring steel members 71 mounted on fore die head 67a. As mandrel 54a advances towards the right (FIGS. 6, 17, and 18) cam 70 will engage members 71 and move them outwardly so that their bent ends will project through apertures 65a and deform blanks 21 to form abutments 25 thereon. As mandrel 54a moves leftwardly after a forming operation, cam 70 is withdrawn to allow members 71 to return to the position shown in FIG. 17.

Turning again to FIGS. 5 and 6, carriage 50 is mounted on bearing blocks 72 which are slideable along rails 73 supported on machine frame 47. Carriage 50 also carries a pneumatic cylinder 74 which is affixed thereto. The cylinder piston 75 is coupled to the cylinder piston 76 of a second cylinder 77 which is rigidly connected to machine frame 47. The arrangement is such that by actuating one cylinder piston rod, e.g., 75, the carriage 50 can be moved a first distance relative to the machine frame, and thereafter a farther distance by actuating the other cylinder piston rod. Also connected to carriage 50 is a cam 80 and a switch actuating pin 81.

A blank supporting table 82 is provided between carriage 50 and sorting table 36. Its purpose is to support a "ready to be formed" blank 21 in position to be engaged by mandrel 54. Table 82 is spaced from the end of sorting table 36 so that a movable plural fore die head 67 can be positioned adjacent the end of a blank 21 delivered to table 82. The die head 67, which carries its own heating unit, is mounted on arms 83, 83a pivotally supported by pillow blocks 84, 84a secured to machine frame 47. The die head 67 is normally positioned between the ends of tables 36 and 82. Arm 83 is extended past pillow block 84 to provide an actuating link 85 for a purpose later to be described. Fore die head 67 is connected to the piston rod 86 of cylinder 87. In its normal position between tables 36 and 82, die head 67 will prevent blanks 21 from sliding out of channels 41 on table 36. The die head will be in this same position when forming one end of ejector tube 22. Die head 67 will, however, be lowered to allow a blank to pass thereover as it is delivered from sorting table 36 to supporting table 82. After a blank is delivered to table 82, die head 67 will be pivotted upwardly so that each die cavity therein is adjacent the end of a blank supported on table 82. As will later be described, carriage 50 will advance to position a mandrel 54 in each blank 21 and thereby form an ejector tube 22.

At the time that die head 67 is pivotted downwardly, the rightwardly extending link 85 engages lever 90 and pivots it and shaft 91, to which lever 90 is keyed, in a counterclockwise direction. Shaft 91 is rotatably supported by standards 93 mounted on machine frame 47. A clamping mechanism comprising three separate clamping bars 94, 94a, and 94b extending, respectively, between arms 95, 95a, and 95b is secured to shaft 91 so that it pivots when the shaft does. The three clamping bars together engage blanks 21 in each channel 41 of sorting table 36.

Figure 14:
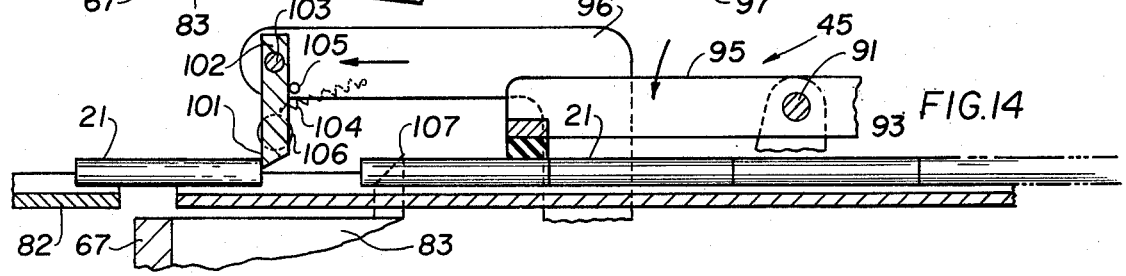
FIG. 14 is a side elevational view of the feeding mechanism during another stage of operation of the apparatus.

The blank clamping mechanism just described is operated in timed relationship with the blank feeding mechanism 45 which delivers one blank 21 from each channel 41 of sorting table 36 to blank supporting table 82 preparatory to that blank being formed into an ejector tube 22. The feeding mechanism 45 comprises a pair of L-shaped arms 96 mounted on platform 97. Platform 97 is located below sorting table 36 so that arms 96 extend upwardly through elongated slots provided in the table between two adjacent channels 41. Platform 97 in turn has secured to its underside, a pair of sliding bearing members 100 that slide on rails 73. Thus, platform 97 can slide along rails 73 carrying arms 96 in a reciprocating fashion. A pusher blade 101 which advances a blank 21 from each channel 41 of table 36 to table 82 is secured to two U-shaped brackets 102, each of which in turn is pivotally connected to an arm 96 by means of a pin 103. Pusher blade 101 is pivotted to a vertical position, as shown in FIGS. 6 and 14, by a spring 104 which biases the blade 101, or more precisely brackets 102, against stop pin 105. The pusher blade 101 has a follower roller 106 provided at each end thereof for cooperation with cams 107 provided on die head arms 83, 83a. The function of rollers 106 and cams 107 will be explained hereinafter when the operation of the apparatus is described.

Platform 97 is reciprocated by a pneumatically operated cylinder 110 and piston, the latter of which is connected to platform 97 by rod 111 and bracket 112.

The last remaining assembly mounted on machine frame 47 is the stripper mechanism 46 which, as has been mentioned, strips formed ejector tubes 22 from mandrels 54 thereby allowing them to fall into a collection hopper (not shown) located below machine frame 47. Mechanism 46 comprises a cross bar 113 extending across the full width of the forming mechanism 44 and connected at each end to an arm 114 pivotally supported in pillow blocks 115 mounted on machine frame 47. Depending from cross bar 113 is a stripping bar 116 having a plurality of semi-circular cut-outs 117 (one for each mandrel 54) separated one from another by the spacing between mandrels 54. The diameter of a cut-out 117 is approximately equal to that of a blank 21. The stripper mechanism 46 will be urged by its own weight to a position determined by an adjustable stop screw 120. A cam follower roller 121 is provided on arm 114.

In operation, hopper 30 will be filled with a supply of tubular blanks 21 and kept supplied as they are discharged to elevator mechanism 31. The elevator mechanism will be operated at a speed to supply tubular blanks to sorting table 36 at a rate consistent with the productivity of forming mechanism 37.

Figure 13:
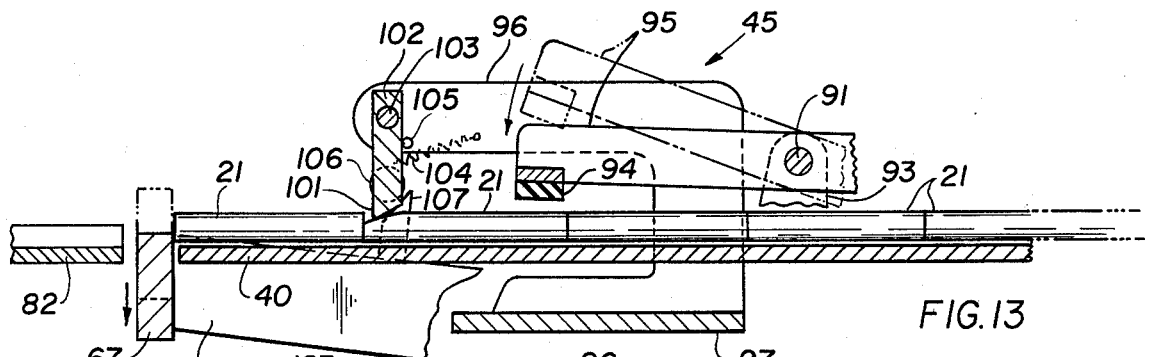
FIG. 13 is a side elevational view of the feeding mechanism during one stage of operation of the apparatus of the invention.

For purposes of the present description of the operation of the apparatus, it will be assumed that the channels 41 of table 36 each have a supply of blanks therein so that for each cycle of operation of the apparatus, a blank 21 will be delivered from channels 41 to table 82. The blank tubes 21 are restrained in the channels 41 by the fore die head 67 which blocks their way out of the channels. See FIG. 13. The apparatus thus is in the condition shown in FIG. 6.

With carriage 50 fully retracted to the left, limit switch 122 is actuated to cause a solenoid valve to admit compressed air into cylinder 77 thereby driving carriage 50 to the right. Carriage will be temporarily arrested with mandrels 54 adjacent supporting table 82. In moving to this position, carriage cam 80 will engage follower roller 121 mounted on stripper mechanism arm 114 and pivot mechanism 46 clockwise so that dies 53 and bracket 52 can pass beneath stripping bar 116.

With rod 76 of cylinder 77 fully extended, carriage 50 actuates switch 123 which controls a solenoid valve to admit compressed air into cylinder 87 and retract rod 86 and thereby pivot fore die head 67 downwardly. As die head 67 moves downwardly link 85 pivots lever 90 counterclockwise to rotate shaft 91 in the same direction and cause clamping bars 94,94a, and 94b to engage the second blank 21 in each channel 41 and thereby restrain all tubes but the first one in each channel from moving. It will be remembered that the tubes move down the channels 41 of table 36 under the influence of gravity.

As fore die head 67 continues its downward movement, and before it clears the leading end of the first blank 21 in each channel 41 of table 36, cams 107 clear follower rollers 106 and allow spring 104 to pivot pusher blade 101 to a vertical position. See FIG. 13. In being so pivoted, the front edge of pusher blade 101 clears the end of the first blank 21 in channel 41 and depresses the leading end of the second blank 21 so that the front edge of blade 101 is behind the first blank 21.

When fore die head 67 clears the bottom of tables 36 and 82, it actuates switch 124 at contact 119 which controls a solenoid valve to admit compressed air into cylinder 110 and drive platform 97 to the left (FIG. 6). Pusher blade 101 thus delivers a blank 21 from each channel 41 of table 36 to table 82. When the blanks are positioned on table 82, switch 125 is actuated by bracket member 126 to arrest platform 97 and return it to its normal position wherein switch 127 is actuated. Actuation of switch 127 causes fore die head 67 to move to the position shown in FIG. 6, that is, with mandrels 54, blanks 21 on table 82, and the die cavities of die head 67 all aligned. During movement of die head to the aligned position, cams 107 pivot pusher blade 101 to the broken-line position shown in FIG. 6 and clamping bars 94, 94a, and 94b are pivotted clockwise thereby releasing blanks 21. The blanks slide down their respective channels under pusher blade 101, which now is pivotted out of their path, and against the rear surface of fore die head 67.

Now, compressed air is admitted to cylinder 74 and carriage 50 advances farther to the right so that mandrels 54 enter the blanks supported on table 82 as shown in FIG. 15. Carriage 50 continues its advance until the mandrels reach the position shown in FIG. 16. At such time the ends of tubular blanks 21 are softened as they are pressed into the heated cavities 53a and 68 to form the outwardly curved continuous bead or rim 24 at the one end and the radially smoothly inturned uninterrupted curve 23 at the other end. Continued advance of carriage 50 causes the arms 63 to press outward against the wall of softened blank 21 to effect the plurality of projections, one for each arm 63, each spaced circumferentially about the tube to define the abutments 25. The ends 23 and 24 and abutments 25 do not affect the wall thickness of the tube which remains substantially uniform throughout, even at the formed projections.

Now, when carriage 50 is returned to its retracted position (FIG. 6) spring 60 will restore pin 61 to its rightward position and arms 63 will be withdrawn within part 56. Also, as cam 80 is withdrawn from under roller 121, stripper mechanism 46 pivots counterclockwise so that stripping bar 116 comes to rest on top of ejector tubes 22. See FIG. 8. The weight of the stripper mechanism on the ejector tubes 22 holds the tubes in an arrested position as mandrels 54 are withdrawn therefrom, whereupon the tubes fall into a collection hopper and stripper mechanism 46 moves to its limiting position as determined by screw 120.

When carriage 50 reaches its fully retracted position, the foregoing cycle of operations is repeated.

Having thus described the invention, it is clear that many other embodiments will suggest themselves to those skilled in the art and these could be provided without departing from the spirit or scope of the invention. For example, hydraulically operated cylinders could be used instead of the pneumatic ones described. A single cylinder could replace cylinders 74 and 77 and the movement of carriage 50 appropriately controlled. Blanks 21 could be fed to table 82 from an overhead feeder so that die head 67 would not have to be pivotted out of their path. Therefore, it is intended that the foregoing description and the drawing be interpreted as illustrative rather than in a limiting sense.

What is claimed is:

1. Apparatus for forming the inner ejector tube of a telescoping tampon applicator comprising, a first die means for shaping one end of a tubular cylinder to form an inwardly turned end wall having a central aperture therein, a second die means for shaping the other end of a tubular cylinder to form an outwardly turned bead-like rim, means for supporting a tubular cylinder with its ends in alignment with said first and said second die means, longitudinal tube feeding means for feeding tubular cylinders one at a time in a longitudinal direction to said supporting means, means for moving at least one of said die means towards the other until the distance separating said die means is less than the length of a tubular cylinder supported therebetween whereby the ends of a tubular cylinder are shaped by said die means to form a tampon applicator tube, means for internally supporting said tubular cylinder when its ends are being shaped by the converging die means, and means for removing a formed ejector tube from said internal supporting means, said die means being heated to soften the tube ends for shaping.

2. Apparatus as in claim 1, said internal supported means being mandrel means integral with one of said die means.

3. Apparatus for forming the inner ejector tube of a telescoping tampon applicator according to claim 1 wherein said means for internally supporting a tubular cylinder comprises mandrel means operable with said second die means and including means for forming abutment means on the outside of a tubular cylinder when it is being formed into an ejector tube.

4. Apparatus for forming the inner ejector tube of a telescoping tampon applicator according to claim 2 wherein said mandrel means comprises a first part integral with said second die means and a second part connected to said first part, said second part having a central cavity, an axial bore extending from said cavity out of said second part, and a plurality of circumferentially spaced apertures extending from the outer surface of said second part to said central cavity, and means for projecting through said spaced apertures to form abutments on the sidewall of a blank supported by said mandrel means.

5. Apparatus for forming the inner ejector tube of a telescoping tampon applicator according to claim 3 wherein said abutment forming means includes a pin axially slideable within said cavity and bore and projecting out of said second part, and a plurality of arms spaced around said pin and pivotally connected thereto, said arms extending at an angle to said pin towards said circumferentially spaced apertures, means for biasing said pin to a first position out of said second part wherein said arms are withdrawn within said second part, the arrangement being such that when the distance between the die means is reduced to form an ejector tube said pin strikes the first die means thereby sliding said pin against said biasing means to thereby move said arms out through the circumferentially spaced apertures to form abutments on the outside surface of an ejector tube being formed.

6. Apparatus for forming the inner ejector tube of a telescoping tampon applicator according to claim 4 wherein said first part of said mandrel means is formed with a conical cam projecting into the central cavity of said second part, and the axial bore of said second part is a wide central aperture, and wherein said abutment forming means includes a plurality of circularly arranged abutment forming members projecting outwardly from the first die means towards the mandrel means in position to pass through said central aperture to be engaged by said conical cam and thereby moved through said circumferential apertures to form abutments on the outside surface of an ejector tube being formed.

7. Apparatus for forming the inner ejector tube of a telescoping tampon applicator according to claim 1 wherein said means for internally supporting a tubular cylinder comprises mandrel means joined to said second die means, and said means for removing a formed ejector tube being operable to remove the same from said mandrel means.

8. Apparatus for forming the inner ejector tube of a telescoping tampon applicator according to claim 1 wherein said first heated die means includes at least two die members arranged in side by side relationship, said second heated die means includes at least two die members in side by side relationship, said tubular cylinder supporting means supports at least two tubular cylinders in side by side relationship, said feeding means feeds at least two tubular cylinders at a time in side by side relationship to said supporting means, and said tubular cylinder internal supporting means supports at least two tubular cylinders in side by side relationship whereby a plurality of ejector tubes are simultaneously formed by the apparatus.

9. Apparatus for forming the inner ejector tube of a telescoping tampon applicator which comprises a downwardly inclined sorting table having a plurality of longitudinal channels for guiding a plurality of rows of tubular blanks downwardly to an ejector tube forming mechanism, an elevator mechanism for carrying tubular blanks to the top of said sorting table, means for directing downwardly falling blanks into the channels of said sorting table, means for restraining tubular blanks in the channels of said sorting table, a first die head means for shaping the forward end of tubular blanks to form an inwardly turned end wall, said first die head having a plurality of die cavities spaced apart a distance corresponding to the separation of the channels of said sorting table, means for said first die head movable out of and into longitudinal alignment with the channels of said sorting table, a second die head having a plurality of die cavities spaced apart a distance corresponding to the separation of the channels of said sorting table and longitudinally aligned therewith, a plurality of mandrels each aligned with a die cavity of said second die head, a tubular cylinder supporting table located between said first and said second die heads, means for simultaneously feeding one tubular cylinder from each channel of said sorting table to said supporting table when said first die head is out of longitudinal alignment with the sorting table channels, means for moving said second die head longitudinally towards said supporting table when said first die head is in longitudinal alignment with the sorting table channels whereby said plurality of mandrels each enter a tubular blank supported on said supporting table and the die cavities of said die heads shape the ends of the tubular blanks to form a plurality of tampon applicator ejector tubes, and means for stripping formed ejector tubes from said mandrels.

10. A mechanism for forming an ejector tube for a tampon applicator comprising a mandrel for insertion into the ejector tube, first die means on said mandrel against which one end of the ejector tube will abut to form a desired shape thereon, second die means spaced from said mandrel against which the opposite end of the ejector tube will abut to form a desired shape thereon, means to move said first and second die means relative to each other for abutment by the respective ends of the ejector tube to shape the same, said first and second die means each being heated to soften the ejector tube at the respective ends thereof to aid in the desired shaping of the ejector tube, means on said mandrel operable during said relative movement of said die means for projection outward from said mandrel into engagement with the ejector tube to press against the inside of the ejector tube and to produce a projection on the outer surface of the ejector tube, and means for removing a formed ejector tube from said mandrel.

11. A mechanism as in claim 10 wherein the ejector tube has a substantially uniform thickness throughout, one of said die means producing a softening of the ejector tube where said operable means engages therewith to enable said operable means to produce a projection on the outer surface of the ejector tube without substantially affecting the thickness of the ejector tube thereat.

* * * * *